United States Patent

Reinhardt et al.

Patent Number: 5,110,574
Date of Patent: May 5, 1992

[54] PRECIPITATED SILICAS AND PROCESS FOR THEIR PRODUCTION AND USE

[75] Inventors: Helmut Reinhardt, Cologne; Adam Becker, Bornheim-Hersel; Robert Kuhlmann, Erftstadt; Peter Nauroth, Wesseling, all of Fed. Rep. of Germany

[73] Assignee: Degussa Aktiengesellschaft, Frankfurt am Main, Fed. Rep. of Germany

[21] Appl. No.: 281,917

[22] Filed: Dec. 7, 1988

Related U.S. Application Data

[63] Continuation of Ser. No. 123,006, Nov. 19, 1987, abandoned.

[30] Foreign Application Priority Data

Nov. 21, 1986 [DE] Fed. Rep. of Germany ....... 3639845

[51] Int. Cl.$^5$ .................... C01B 33/12; C09K 3/14; A61K 7/16
[52] U.S. Cl. ..................... 423/335; 51/308; 51/311; 423/339; 424/49; 424/52
[58] Field of Search ............... 51/308, 311; 423/335, 423/339; 424/49, 52

[56] References Cited

U.S. PATENT DOCUMENTS

| | | | |
|---|---|---|---|
| 3,235,331 | 2/1966 | Nauroth et al. | 423/339 |
| 3,433,593 | 3/1969 | Reinhardt et al. | 423/339 |
| 3,864,470 | 2/1975 | Watson | 424/49 |
| 3,928,541 | 12/1975 | Wason | 423/339 |
| 4,001,379 | 1/1977 | Türk et al. | 423/335 |
| 4,003,981 | 1/1977 | Türk et al. | 423/339 |
| 4,122,161 | 10/1978 | Wason | 424/49 |
| 4,340,584 | 7/1982 | Wason | 424/54 |
| 4,356,107 | 10/1982 | Payne | 51/308 |
| 4,420,312 | 12/1983 | Wason | 51/308 |
| 4,421,527 | 12/1983 | Wason | 51/308 |
| 4,495,167 | 1/1985 | Nauroth et al. | 423/339 |

FOREIGN PATENT DOCUMENTS

| | | |
|---|---|---|
| 1293138 | 4/1969 | Fed. Rep. of Germany . |
| 1467019 | 7/1970 | Fed. Rep. of Germany . |
| 3114493 | 10/1982 | Fed. Rep. of Germany . |

Primary Examiner—A. Lionel Clingman
Assistant Examiner—Linda D. Skaling
Attorney, Agent, or Firm—Beveridge, DeGrandi & Weilacher

[57] ABSTRACT

Process for the production of cleansing, polishing and thickening silica for use in toothpastes, which is characterized in that using the conventional precipitation processes, silica suspensions are obtained of various particles sizes and particle densities and are mixed thoroughly together until the mixture is homogenous in the suspension phase and the resulting suspension mixture is treated in the conventional manner by filtering, drying and comminuting.

10 Claims, 2 Drawing Sheets

PRECIPITATED SILICAS AND PROCESS FOR THEIR PRODUCTION AND USE

This application is a continuation of application Ser. No. 123,006 filed Nov. 19, 1987, now abandoned.

The invention relates to precipitated silicas, processes for production and their use in toothpastes.

INTRODUCTION AND BACKGROUND

Synthetically produced precipitated silicas have for many years played an important role as a component part of toothpaste agents. They are very pure, toxicologically satisfactory and compatible with the other component materials of toothpastes, such as for example glycerin, sorbitol, thickening agents, detergents, coloring and fragrance materials and, optionally, soluble fluoride compositions.

Synthetic precipitated silicas are produced by precipitation from alkaline silicate solutions with acids, along with stirring and filtering out of the suspension, washing, drying and comminuting. The precipitating process allows the possibility of predetermining important properties such as the particle diameter, particle shape and particle density and/or hardness, simply by treatment in the flocculating phase.

SUMMARY OF THE INVENTION

It is an object of the invention to provide a process for the production of cleaning, polishing and thickening precipitated silicas for use in toothpastes, which process is characterized in that silicas of various particle sizes and particle densities, which are obtained in the conventional manner by precipitation processes, are then subsequently mixed thoroughly and homogeneously together in the suspension phase and the resulting homogeneous mixture is further treated in the conventional manner by filtration, washing, drying and comminuting.

Another object of the invention resides in providing a precipitated silica, which is characterized by the following physical-chemical features:

| | | |
|---|---|---|
| drying loss (DIN 53198) | % | 3–7 |
| conductivity at 25° C. (4% slurry) | μS | 400–800 |
| pH level (5% accd. to DIN 53200) | | 6–7 |
| BET surface area (DIN 66131) | m²/g | 130–150 |
| tamping density (DIN 53194) | g/l | 100–150 |
| macropore volume D > 30 nm (by Hg injection method) | ml/g | 3.2–4.0 |
| Gardner oil adsorption | ml/100 g | 180–200 |
| water retention capacity | % | 76–79 |
| Cu abrasion | mg | 5–14 |
| RDA abrasion | | 35–100 |
| REA abrasion | | 40–90 |
| scratch test | | little-very little |
| viscosity (in 16% glycerin-water dispersion (1:1); aerometer D with heliopath) | mPas | 5000–10000 |
| Fe content | ppm | 240–280 |

Another object of the invention is to provide a process for the production of the precipitated silica, which is characterized by the following physical-chemical features:

| | | |
|---|---|---|
| drying loss (DIN 53 198) | % | 3–7 |
| conductivity at 25° C. (4% slurry) | μS | 400–800 |
| pH level (5% accd to DIN 53200) | | 6–7 |
| BET surface area (DIN 66131) | m²/g | 130–150 |
| tamping density (DIN 53194) | g/l | 100–150 |
| macropore volume D > 30 nm (by Hg injection method) | ml/g | 3.2–4.0 |
| Gardner oil absorption | ml/100 g | 180–200 |
| water retention capacity | % | 76–79 |
| Cu abrasion | mg | 5–14 |
| RDA abrasion | | 35–100 |
| REA abrasion | | 40–90 |
| scratch test | | little-very little |
| viscosity (in 16% glycerin-water dispersion (1:1): aerometer D with heliopath) | mPas | 5000–10000 |
| Fe content | ppm | 240–280 |

The process is carried out utilizing two different precipitated silica suspensions which are mixed together and a silica product is recovered which is different from either of the two precipitated silicas that were mixed together.

In one step of the process, a thickening precipitated silica suspension is produced by a conventional conversion reaction of an alkali silicate solution with an acid while avoiding formation of a gel. The alkali silicate solution and the acid are fed simultaneously into a given aqueous alkali silicate solution. The acid and the alkali silicate solution are fed in at certain solution concentrations and certain feed velocities with maintenance of a precipitation temperature of between 80° C. and 90° C. in the reaction medium. The precipitation of the silica takes place in a given alkali silicate solution with a concentration of approximately 5 to 25 g of $SiO_2$ per liter of solution, in such a manner that the viscosity of the reaction medium is held uniformly low during a time period of a least 30% of the total precipitation time period and the pH level is held between 10 and 12. The addition of the reaction components is terminated before the viscosity has dropped, following passage through a maximum, to a value that is less than 100% over the initial viscosity. The pH level thereafter is adjusted with sulfuric acid to below 7.

In another step of the process, an abrasive precipitated silica suspension is produced. To produce the abrasive precipitated silica an original precipitated silica suspension is first obtained by precipitation of silica from a given alkali silicate solution having a concentration of about 5–25 g $SiO_2$ per liter of solution with an acid and alkali metal silicate solution with certain solution concentrations and certain feed velocities. The precipitation temperature is maintained between 80° C. and 90° C. in the reaction medium. If necessary, the mixing vessel contents are thoroughly sheared by agitation during the entire precipitation time. The viscosity of the reaction medium is held uniformly low during a time period of at least 30% of the entire precipitation time and the pH level is held between 10 and 12. The addition of the reaction components is terminated before the viscosity of the system following passage through a maximum falls to a value of less than 100% over the initial viscosity. The resulting product is termed an original precipitated silica suspension.

Thereafter the original precipitated silica suspension is converted to an abrasive precipitated silica suspension. Thus, the pH level of the suspension is then adjusted to 7 to 9 with sulfuric acid. It is then diluted with hot water to a precipitated silica content of from 10–30 g/l and a sodium sulfate content of from 6–20 g of $Na_2SO_4$, and is heated to 80° C. to 90° C. While holding this pH constant, a simultaneous feed of alkali metal silicate solution, sulfuric acid and, if necessary, hot water is introduced into the suspension for a precipitation time of 15 to 180 minutes to obtain a precipitated silica final concentration of from 40 to 80 g/l. Then acidified with sulfuric acid to a pH level below 7. The resulting product is termed an abrasive precipitated silica suspension.

Thereafter, both precipitated silica suspensions; i.e. the thickening precipitated silica suspension and the abrasive precipitated silica suspension, are thoroughly mixed together. The resulting precipitated silica is filtered out, washed, spray-dried and then comminuted in an air spray mill.

In one preferred embodiment of the invention, the thickening silica suspension is produced essentially as in German Auslegeschrift 14 67 019 corresponding to U.S. Pat. No. 3,235,331 the entire disclosure of which is relied on and incorporated by reference. The abrasive precipitated silica suspension is preferably produced essentially as in German 31 14 493, Example 10.

Another object of the invention is to provide a precipitated silica characterized by the following physical-chemical characteristic features:

| | | |
|---|---|---|
| drying loss (DIN 53198) | % | 3–7 |
| conductivity at 25° C. (4% slurry) | μS | 250–400 |
| pH level (5% accd. to DIN 53200) | | 6–7 |
| BET surface area (DIN 66131) | m²/g | 220–250 |
| tamping density (DIN 53194) | g/l | 80–120 |
| macropore volumes D > 30 nm (by Hg injection method) | ml/g | 3,2–4.0 |
| Gardner oil absorption | ml/100 g | 200–220 |
| water retention capacity | % | 77–78 |
| Cu abrasion | mg | 8–12 |
| RDA abrasion | | 60–80 |
| REA abrasion | | 60–90 |
| scratch test | | little |
| viscosity (in 16% glycerin-water dispersion (1:1); aeromater D with heliopath) | mPas | 14000–18000 |
| Fe content | ppm | 70–90 |

Still another object of the invention is to provide a process for producing a precipitated silica characterized by the following physical-chemical characteristic features:

| | | |
|---|---|---|
| drying loss (DIN 53198) | | 3–7 |
| conductivity at 25° C. (4% slurry) | μS | 250–400 |
| ph level (5% accd. to DIN 53200) | | 6–7 |
| BET surface area (DIN 53200) | m²/g | 220–250 |
| tamping density (DIN 53194) | g/l | 80–250 |
| macropore volumes D > 30 nm (by Hg injection method) | ml/g | 3,2–4.0 |
| Gardner oil absorption | ml/100 g | 200–220 |
| water retention capacity | % | 77–78 |
| Cu abrasion | mg | 8–12 |
| RDA abrasion | | 60–80 |
| REA abrasion | | 60–90 |
| scratch test | | little |
| viscosity (in 1:1 16% glycerin-water dispersion, aeromater D with heliopath) | mPas | 14000–18000 |
| Fe content | ppm | 70–90 |

The process is carried out by first preparing two different precipitated silica suspensions and then mixing the two suspensions together to form the desired product.

To prepare one of the two suspensions, an abrasive precipitated silica suspension is formed, starting with an original precipitated silica suspension. This starting material is produced by precipitation of silica from a given alkali silicate solution with a concentration of approximately 5 to 25 g of $SiO_2$ per liter solution using an acid and alkali metal silicate solution with certain selected solution concentrations and certain feed velocities. The precipitation is carried out while maintaining a precipitation temperature of between 80° C. and 90° C. in the reaction medium, so that the viscosity of the reaction medium is held uniformly low for a time period of at least 30% of the entire precipitation time period and the pH is held between 10 and 12. The addition of the reaction components is terminated before the viscosity following passage through a maximum falls to a level lower than 100% over the initial viscosity.

This original precipitated silica suspension is then converted to an abrasive precipitated silica suspension by adjusting the pH level with sulfuric acid to 7 to 9. The reaction medium is then diluted with hot water to a precipitated silica content of from 10–30 g/l and sodium sulfate content of from 6–20 g of Na $SO_4$/liter, and is heated to 80° C.–90° C. The pH is adjusted with sulfuric acid to 7 to 9.

While holding this pH content, alkali metal silicate solution, sulfuric acid and if necessary hot water, are simultaneously fed in over a precipitation time period of from 15 to 180 minutes. The resulting precipitated silica final concentration is from 40 to 80 g/l. The suspension so obtained is acidified with sulfuric acid to a pH level below 7. The resulting product is identified as an abrasive precipitated silica suspension.

To prepare the second precipitated silica suspension, the precipitation of the silica is carried out in a strongly acidic pH environment, preferably at a pH of between 1.5 and 2.5. As is known in the art, a simultaneous feed of sodium silicate and acid solutions is conveyed to a preparation of starting materials dissolved in water, which form complex compositions which are soluble in combination with iron.

Both precipitated silica suspensions, i.e., the abrasive precipitated silica suspension and the second precipitated silica suspension, are then mixed thoroughly together, the precipitated silica is filtered out, washed, spray-dried and then comminuted using an air jet mill.

In one preferred exemplary embodiment, the abrasive precipitated silica suspension is produced essentially as in German OLS 31 14 493, Example 10. The other (second) precipitated silica suspension is preferably produced according to German Patent 12 93 138, in which the substances used therein as chelating agents are preferably sodium fluoride and oxalic acid.

BRIEF DESCRIPTION OF THE DRAWINGS

The present invention will be further understood with reference to the drawings wherein.

DETAILED DESCRIPTION OF THE INVENTION

It has been discovered by applicants that by mixing precipitated silicas of various distinctly different properties in the suspension phase, especially valuable precipitated silicas are obtained for incorporation into toothpaste formulations. Suitable precipitated silica suspensions can be obtained directly by precipitation or by reslurrying of the press cake from the precipitated silica filter press. Precipitated silica suspensions obtained directly by precipitation are preferable.

The precipitated silicas obtained according to the invention by mixing of precipitated silica suspensions, filtering, drying and comminuting have more favorable properties in toothpastes than dry mixtures of the same original silica components in the same proportions.

Figure 1:
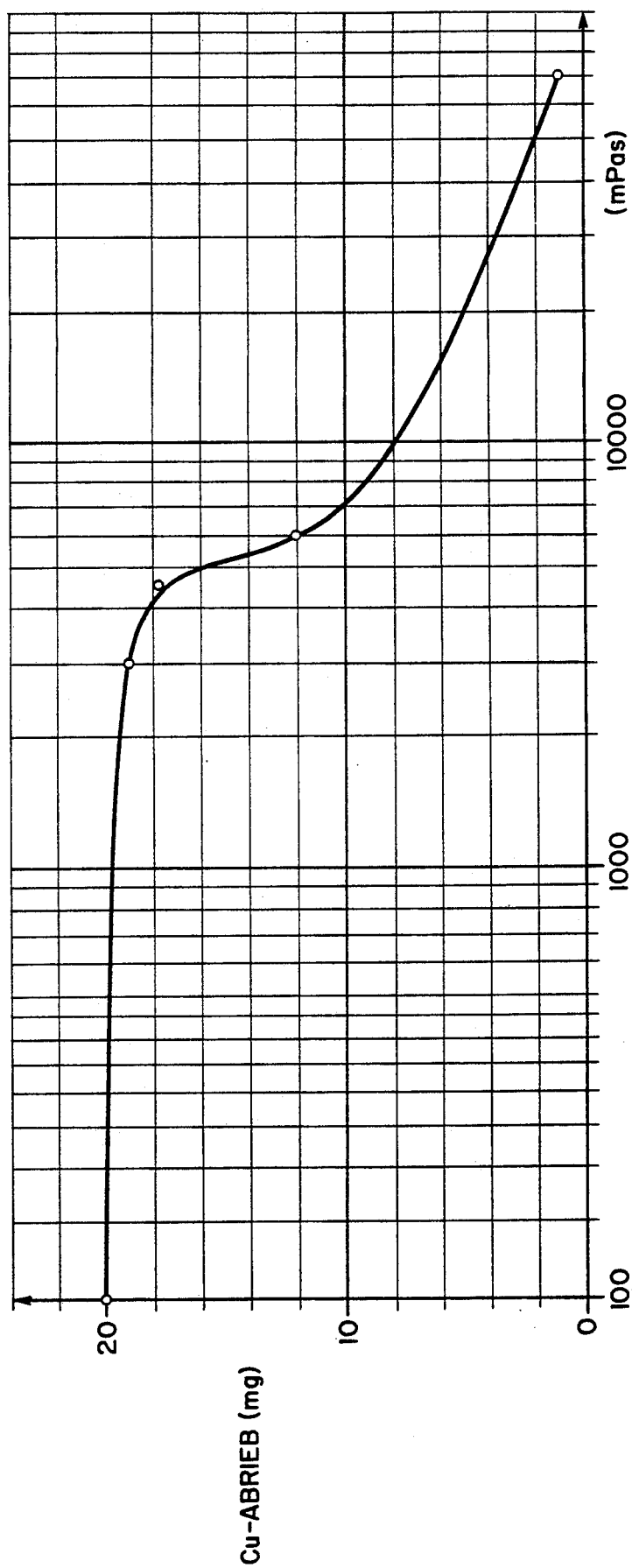
FIG. 1 is a graph of change in abrasiveness with viscosity.

The precipitated silicas according to the invention show synergistic effects of such a type that an unexpected degree of abrasiveness occurs with the given viscosity and/or thickening effect, in other words, the viscosity-abrasiveness correlation surprisingly is not linear in effect. This is seen by reference to FIG. 1.

The precipitated silicas according to the invention can advantageously be produced quite easily, because the quantities of materials can be adjusted either continuously or in stages relative to suitable volumes or weights using known solid material contents. Furthermore the wetting process advantageously raises no dust problems. Also, incidents of separation are minimized. Apparently the components in the wet suspensions as contrasted to the dry mixtures lose some of their separate identities. It is believed that interactions of smaller with larger particles occur with the thorough mixing and supposedly especially with the drying, and the small particles are accumulated or actually grow on larger particles.

Also, different shapes or forms of flocculation and permeability are to be taken into consideration in the aqueous phase.

Figure 2:
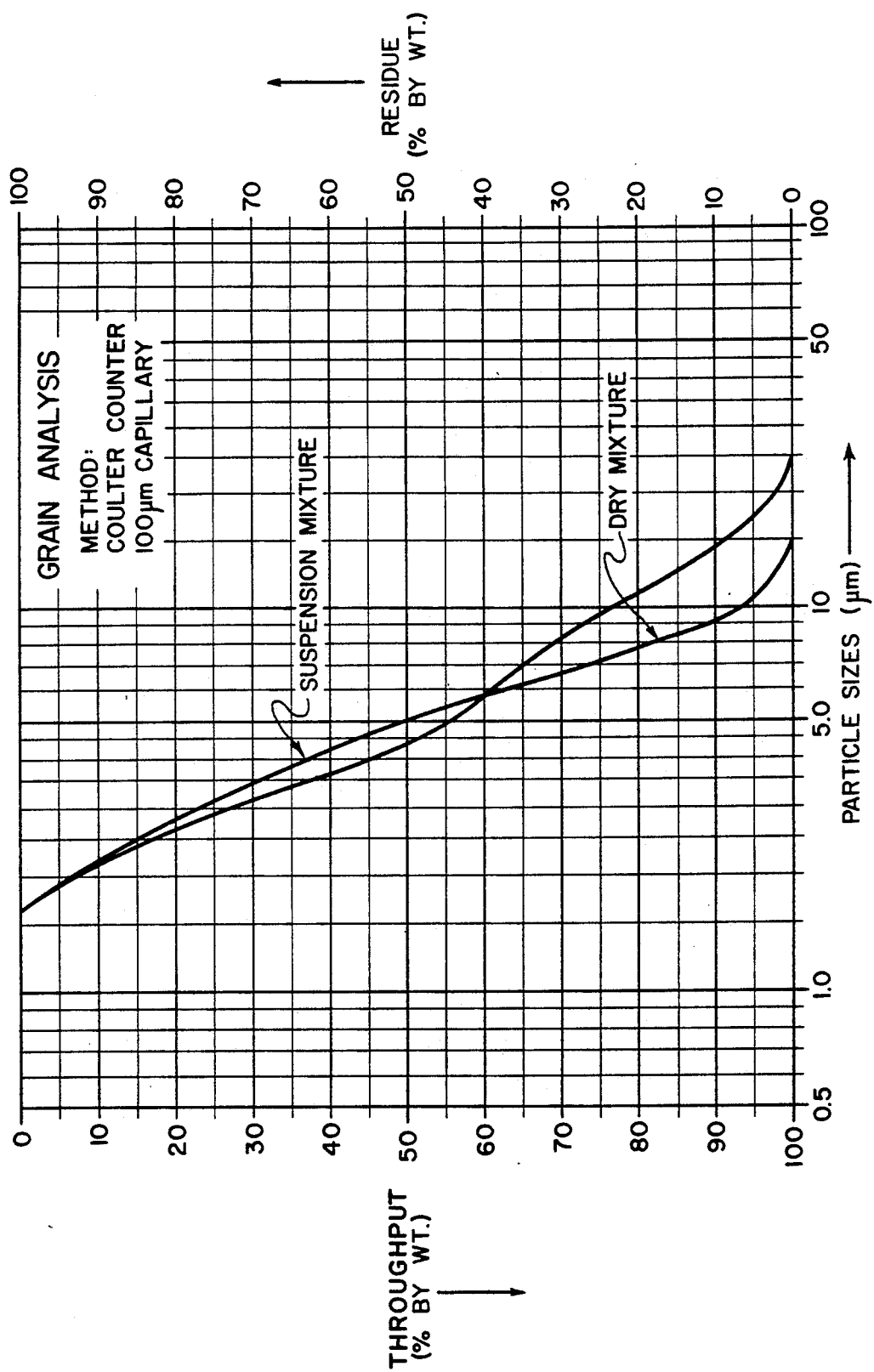
FIG. 2 in a graph showing throughput and residue as a function of particle size as determined by the Coulter Counter method.

A first clear differentiation between dry and wet mixing arises from the particle size distribution of the comminuted samples. During the dry mixing of two precipitated silicas with different particle sizes and densities, the Coulter Counter measurement, as expected, shows 2 maximums and the corresponding curve has a hump, the curve runs through the identical precipitated silicas, mixed together wet in identical proportions, in complete compatibility (see FIG. 2).

Another notable difference resides in the thickening effect. The precipitated silica according to the invention increases the viscosity of a control mixture of glycerin and water notably less than does the dry mixture.

Precipitated silicas with more moderate thickening capacity allow greater filler content and, hence, the production of toothpastes with a "full" character.

On the other hand, pastes with lower filler content feel "thin" or "watery" in the mouth.

The thickening effect of the precipitated silica must evolve completely during its working into the toothpaste mass, in other words there can thereafter be no change or modification of the rheological proportions of the toothpaste, which would make the filling and eventual emptying of the tubes and container more difficult or even quite impossible.

Basically a toothpaste is intended to aid or increase the cleaning capacity and efficiency of the toothbrush, and for this a film is built up between brush and tooth surface, which mechanically removes the coatings from teeth.

This can be provided only by a medium which contains some abrasive properties.

With identical REA scouring or abrasion performance, of course, the precipitated silicas which produce the least scratching are to be preferred.

The precipitated silicas according to the invention actually combine in an advantageous manner the requirements for stable viscosity development at mid-levels with greater abrasive and cleaning effect while avoiding deep scratching.

The measurement of the abrasiveness is implemented by means of the use of extracted human teeth which are made radioactive, on free dentin (RDA level) or an enamel (REA level). The level of absorption of radioactivity by the suspension of the toothpaste mixture to be tested is also measured following predetermined brushing of the test teeth.

As an alternative for that testing practice, the loss in weight of copper plates can be ascertained during the brushing with suspension samples. The values which are thus obtained, however, frequently cannot be compared with RDA and REA values.

In special laboratories, finely divided samples, for instance microscopic samples, are analyzed for the cleaning and polishing effect of toothpaste agents. Samples which exhibit many scratches or deep scratches are separated out. These tests are carried out on extracted animal or human teeth.

An impression of the size and number of scratches produced by a toothpaste agent has already been obtained by microscopic or stereomicroscopic observation of definitively treated metal plates, such as is accumulated for example in the measurement of copper abrasion.

In addition to the thickening properties and the esthetic cleaning and polishing effect, a high level of purity in relation to heavy metal content is also expected in recent times from a precipitated silica, for reasons of good health and safety. Higher iron content could therefore lead to the more intense and undesired coloring of the pastes, which are formulated to transparent, partially colored compositions. For example, a paste which is colored with indigo blue can turn into a greenish distorted shade because of the iron content of the silica.

We have now made a further discovery that during the course of the wet mixing, with selection of certain silicas very pure products can be obtained with especially low iron content.

Another object of the invention is the use of the precipitated silica obtained according to the invention as abrasive and/or polishing agent in toothpastes.

The following examples are illustrative of additional details of the invention.

The solid content (precipitated silica content) of the precipitated silica suspension is ascertained as follows:

250 ml of the precipitated silica suspension which is cooled to 20° C. are drained off and filtered on a porcelain filtering flask (diameter 120 mm) and then the filter cake is washed within 500 ml of electrolyte-poor water. The cake is dried at 105° C. until it reaches a constant weight.

Summary: g/weighed product $\times 4 =$ g/solid material/1

EXAMPLE 1

A precipitated silica with thickening effect is produced essentially according to the process in German Auslegeschrift 14 67 019, corresponding to U.S. Pat. No. 3,235,331 relied on and incorporated herein.

As a modification to the process described in U.S. Pat. No. 3,235,331 and for economical reasons, concentrated sodium silicate solution (density - 1.353 g/ml) and concentrated sulfuric acid (96)% are used. The resulting a solid material content in the precipitated silica suspension is 85 g/l.

In a rubber-lined 120-liter precipitation vessel, 73 liters of hot water and 5.25 liters sodium silicate solution (density = 1.353 g/ml, ratio $SiO_2: Na_2O = 3.46$) are heated to 85° C. with stirring. During the next 90 minutes 16.5 liters sodium silicate solution (density = 1.353 g/ml, ratio $SiO_2: Na_2O = 3.46$) at a rate of 11.0 liters/hour and 1.448 liters sulfuric acid (96%) are simultaneously dosed in at a rate of 0.965 liters/hour into this alkali precipitate vessel with stirring and with maintenance of the temperature at 85° C. The addition of the reaction components is terminated before the viscosity has dropped to a value less than 100% over the initial viscosity.

Then the silica precipitate suspension is adjusted with (96%) sulfuric acid to a pH of 3.5, which is attained by an acid addition of several minutes at a rate of 1.25 liters/hour. The precipitated silica suspension which is obtained in this manner has a solid material content of 85.0 g/l.

The precipitated silica which is obtained after filtering out, washing out, spray drying and comminuting in the air jet mill has the physical-chemical features listed in Table 1.

EXAMPLE 2

This example describes the production of an abrasive precipitated silica according to German Offenlegungsschrift 31 14 493, Example 10, (relied on and incorporated by reference) but with the modification that the entire volume of water is introduced into the precipitation vessel, whereupon the water imput during the precipitation is eliminated, and the precipitation time is extended from 60 to 100 minutes.

In a rubber-lined 120-liter precipitation vessel, 73 liters of hot water and 5.25 liters of sodium silicate solution (density = 1.353 g/l; ratio: $SiO_2: Na_2O = 3.46$) is heated to 85° C. with stirring. Then 16.5 liters of sodium silicate solution (density = 1.353 g/ml; $SiO_2:Na_2O = 3.46$ modulus) at a rate of 11.0 liters/hour together with 1.448 liters of concentrated (96%) sulfuric acid at a rate of 0.965 liters/hour are dosed simultaneously into this alkaline precipitation vessel for the following 90 minutes with stirring and with maintenance of the temperature at 85° C. Input of the reaction components is terminated before the viscosity of the reaction medium has dropped following passage through a maximum to a value less than 100% over the initial viscosity.

Then the precipitated silica suspension which is thus obtained is adjusted with the addition of concentrated (96%) sulfuric acid to a pH of 8.5, which takes place as a result of an acid addition at a rate of 1.25 liters/hour for a period of several minutes. The precipitated silica suspension which is thus obtained has a solid material content of 85 g/l and a $Na_2SO_4$ content of 55 g/l.

During the entire 90 minutes of precipitation time the suspension is sheared intensively by means of a centrifugal pump which swirls the contents of the container many times. More precise data relative to the apparatus which is used and relative to the shear conditions is found in German Patent 17 67 32 and especially therein in column 8, lines 31–68.

The original precipitated silica suspension which is produced in this manner is adjusted with water to a precipitated silica content of 13 g/l and 8.5 g of $Na_2SO_4$/liter. Then 16.06 liters of this suspension are heated to 85° C. in a rubber-lined 120-liter precipitation vessel with stirring. Then 23.1 liters of sodium silicate solution (density = 1.353 g/ml; ratio $SiO_2: Na_2O = 3.46$) at a rate of 231.0 ml/min together with 1.94 liters of sulfuric acid (96%) at a rate of 19.4 ml/minute are added simultaneously to the precipitated silica suspension with maintenance of this temperature and a pH of 8.5 for a period of 100 minutes. The precipitated silica suspension is then adjusted to a pH of approximately 3.5 with (96%) sulfuric acid. The precipitated silica suspension which is obtained has a solid material content of 92.0 g/l.

The precipitated silica obtained following filtering and washing out has the physical-chemical features listed in Table 1 under Example 2.

EXAMPLE 3

18.5 cubic meters suspension of the abrasive precipitated silica suspension with a precipitated silica content of 92.0 g/l made in Example 2 are mixed with 40.0 cubic meters suspension of a precipitated silica thickener made in Example 1 with a precipitated silica content of 85.0 g/l and corresponding to a weight ratio of 1 : 2 (measured in terms of the precipitated silica content).

For further treatment, the precipitated silica of this suspension mixture is separated out by means of filter presses. The precipitated silica content in the filter press pulp amounts to 24%. The washed and spray-dried filter press pulp is comminuted in an air jet. The precipitated silica which is obtained has the physical-chemical features listed in Table 1 under Example 3.

EXAMPLE 4

1.0 kg of washed, dried and comminuted precipitated silica thickener of Example 1 is dry mixed with 2.0 kg of the likewise and in a comparable manner washed, dried and comminuted precipitated silica abrasive of Example 2. The weight ratio of the two precipitated silicas is the same as in Example 3, viz. 1 : 2.

The precipitated silica which is obtained has the physical-chemical features which are listed in Table 1 under Example 4.

EXAMPLE 5

As a first step, a precipitated silica abrasive is produced according to the conditions of German Offenlegungsschrift 31 14 493.4, Example 12, as follows:

In a precipitating vat provided with a stirring apparatus 27.0 cubic meters of hot water and 10.0 cubic meters of precipitated silica suspension prepared essentially as described in German 14 67 019, which is acidified only to pH 8.5, with a precipitated silica content of 85 g/l are mixed and heated to 85° C. As a modification of German Auslegeschrift 14 019, for economic reasons, concentrated sodium silicate solution (density = 1.353 g/ml) and concentrated (96%) sulfuric acid are used. In this case a solid material content of 85 g/l in the precipitated silica suspension results. At this temperature and with maintenance of a pH of 8.5–9, 9.6 cubic meters of sodium silicate solution (density = 1.353 g/ml; ratio $SiO_2O: Na_2O = 3.46$), 0.94 cubic meters of concentrated (96%) sulfuric acid and 20 cubic meters of hot water are added simultaneously for a period of 80 minutes.

After the precipitation has ended, the suspension is brought to a pH of 3.5 with addition of concentrated (96%) sulfuric acid. The precipitated silica content amounts to 66.0 g/l.

25.75 cubic meters of this precipitated silica suspension are mixed with 40.0 cubic meters of suspension of a silica thickener produced according to Example 1 with a precipitated silica content of 85.0 g/l which corresponds to a weight ratio of 1 : 2, (based on the solid material content).

Further treatment is accomplished as described in Example 3. The silica content in the filter press pulp amounts to 21%.

The precipitated silica which is obtained has the physical-chemical features listed in Table 1.

EXAMPLE 6

A precipitated silica which is low in iron is produced as in Example 1 of D 47 633 (=German patent 12 93 138).

18.5 liters of water are introduced into a 30 liter cylindrical wooden container, which is provided with a wooden blade mixer (diameter 20 cm, height 6 cm, 90 rpm).

The water is heated indirectly to 85° C. with a steam coil of acid-resistant steel and then 25 g of sodium fluoride and 6.25 g of oxalic acid are dissolved in the water.

Then 5.45 liters of commercial sodium waterglass (mole ratio of $Na_2O$: $SiO_2$= 1: 3.36, density=1.34) and 0.55 liters (96%) sulfuric acid are added at points which are diametrically opposite each other, with stirring and while maintaining a pH of 2.0 for 90 minutes.

The suspension which is formed is stirred for another 30 minutes. Then it is filtered in a known manner in filter flasks, washed with twice the volume of water, measured on the volume of the suspension, spray dried and comminuted using an air jet.

EXAMPLE 7

18.2 cubic meters of an abrasive silica suspension made according to Example 2 with a precipitated silica content of 92.0 g/l are then mixed with 40.0 cubic meters of a precipitated silica suspension which is low in iron and made according to Example 1 of D 47 633 (=German Patent 12 93 138) with a precipitated silica content of 83.8 g/l, corresponding to a weight ratio of 1 : 2.

For further treatment, one proceeds as described in Example 3. The silica content in the press pulp amounts to 23%.

The precipitated silica which is obtained has the physical-chemical features which are listed in Table 1.

EXAMPLE 8

A suspension of silica which is low in iron, produced according to Example 1 of German Patent 12 93 138 (=D 47 633) is mixed with a suspension of abrasive silica material produced according to the above Example 2 in certain quantities and ratios in order to produce a precipitated silica which is low in iron and which possess thickening and cleaning properties. Table 2 shows that the iron content of the mixture with each weight ratio is lower than that of the comparable dry mixture.

TABLE 2

| | Mixture ratios in parts by weight | | |
|---|---|---|---|
| Silica abrasive material, as described | 2 | 1 | 1 |
| Silica low in iron as in Ex. 1 of D 47 633 | 1 | 1 | 2 |
| Wet mixture | 157 ppm | 118 ppm | 80 |

TABLE 2-continued

| | Mixture ratios in parts by weight | | |
|---|---|---|---|
| Dry mixture | Fe 168 ppm Fe | Fe 137 ppm Fe | Fe 101 Fe |

The physical-chemical features which are described herein are determined as follows:

Dry loss
according to DIN 53 198.
Conductivity at 25° C.
/4% slurry

A suspension sample of 4.0 g is heated with 50 ml of completely softened water in a 150-ml glass beaker and is boiled for one minute with stirring. Then the suspension is transferred into a 100-ml flask, cooled and filled up to the mark with completely softened water. The electrical conductivity is measured with a commercial meter, for instance the "Wissenschaftlich-Technischen Werkstatten" (WTW), LF type Conductometer, at 25° C.

pH level In 5% aqueous dispersion, according to DIN 53 200 BET surface area according to DIN 66 131

A sample is rinsed with nitrogen at 100° C. The volumetric measurement is carried out with pure nitrogen at the temperature of liquid nitrogen (−195.8° C.)

Tamping density according to DIN 53 194

The test is undertaken without pretreatment of the sample.

Macropore volume D>30 nm
by the Hg injection method

The measurement occurs by means of the Mercury Pressure Porosimeter, 200 Series, of the Carlo Erba Strumentazione company.

Gardner-Colemen oil absorption
according to ASTM : D 1483-60
Water retention capacity The water retention capacity, after pressing down the precipitated silica suspension and washing out electrolyte to a low content, indicates the water portion contained in the press pulp. For the determination, 250 g of press pulp are dried to uniform weight at 105° C.

Summary of calcualtions $$100 - \frac{\text{Weight of product} \times 100}{\text{weight of initial sample}} = \% \text{ water retention capacity}$$

Particle size distribution
according to Coulter Counter/100 micrometer Kap.

The measurement occurs with the Coulter Counter Model TA II of the Coulter Electronics GmbH company.

Determination of the Cu abrasion in 10% glycerin dispersion
a) Production of the glycerin dispersion 153 g of glycerin (water-free, purest pH Eur, BP USP, density=1.26 g/ml, by Merck of Darmstadt), are weighed in a polyethylene flask (250 ml). Then 17 g of precipitated silica are carefully folded in with a spatula. The mixture is then homogenized with a paddle-stirrer (diameter 5.2 cm) for 12 minutes at the rate of 1500 rpm.

b) Implementation of the abrasion measurement

The determination of the degree of abrasion is by means of the abrasion test device, which is known from the following publications: (1) Pfrengle: Fat, Soaps, Spreading Agents, 63 (5) (1961), pages 445 to 451

"Abrasion and Reinigungskraft von Putzkoerpern in Zahnpasten", (2) A. RENG, F. DANY; Parfuemerie and Kosmetick 59 (2) (1978), pages 37 to 45; "Anwendungstechnische Pruefung von Zahnpasten".

The 6 troughs of the test apparatus which were coated with 20 ml each with the homogeneous dispersion. Six surface-ground nylon brushes on six surface-ground Cu plates (electrolytic copper) work for five hours with 50,000 double strokes, is the abrasion determined by measurement of the differential in weight. With the computation of the abrasiveness, average values are formed from the values which are obtained. The DE OS 17 67 332 corresponds to U.S. Pat. Nos. 4,003,981 and 4,001,379.

All of the above U.S. documents are relied on an incorporated by reference.

It has been determined that good results are obtained when the suspensions as described above are mixed together for at least about 3 hours to obtain a desired uniform composition.

Further variations and modifications of the foregoing will be apparent to those skilled in the art and are intended to be encompassed by the claims appended hereto.

TABLE 1

|  |  | Ex. 1 | Ex. 2 | Ex. 3 | Ex. 4 | Ex. 5 | Ex. 6 | Ex. 7 |
|---|---|---|---|---|---|---|---|---|
| Drying loss (DIN 53198) | % | 5 | 5 | 5 | 5 | 5 | 5 | 5 |
| Cond. at 25° C. 4% slurry | µS | 730 | 460 | 740 | 650 | 680 | 250 | 290 |
| pH (5%, DIN 53 200) |  | 6.3 | 6.9 | 6.3 | 6.4 | 6.3 | 6.1 | 6.5 |
| BET surf. area (DIN 66131) | $m^2/g$ | 185 | 40 | 140 | 145 | 148 | 310 | 235 |
| Tamp. dens. (DIN 53194) | g/l | 80 | 240 | 130 | 120 | 110 | 80 | 100 |
| Macropr vol. D > 30 nm (Hg inj.) | ml/g | 3.8 | 1.1 | 3.0 | 3.6 | 3.8 | 3.5 | 2.8 |
| Gardner oil absrptn. | ml/100 g | 280 | 80 | 184 | 215 | 195 | 300 | 200 |
| Water ret. cap. | % | 80 | 56 | 76 | — | 79 | 84 | 81 |
| Cu abrasion | mg | 1 | 20 | 12 | 13 | 5 | 1 | 9 |
| RDA abrasion |  | 23 | 170 | 80 | 100 | 35 | 15 | 70 |
| REA abrasion |  | 25 | 130 | 70 | 40 | 45 | 20 | 75 |
| Scratch |  | very littl | much | little | much | very litl | very lit. | little |
| Viscosity (16% glyc./H2O disp. 1:1 aeromtr D with heliopath) | mPas | 72000 | <100 | 6000 | 10800 | 9500 | 170000 | 16500 |
| Fe content | ppm | 260 | 240 | 240 | 260 | 250 | 35 | 80 | abrasion (abrasiveness) is given in mg of Cu.

RDA -abrasion

The RDA method is described in the Journal of Dental Research 55 (4), 563 (1976), and is also used for the REA-abrasion test Scratch Test Scratches are observed visually be means of microscope.

Determination of the viscosity

The viscosity is measured in a 16% glycerin/ water dispersion (1 : 1 mixture) with Brookfield-Viscosimeter RTV, Aerometer 10, with heliopath at 10 rpm.

1. Test sample composition 48 g silica
126 g glycerin (approximately 87%, purest pH Eur. BP, density = 1.23 g/ml; of Merck, Darmstadt
126 g distilled water
300 g 16% dispersion of silicic acid 2. Test Process The silica abrasive material was stirred manually with a glass rod in a 400-ml glass beaker (broad shape) into the glycerin/water mixture (for 1 minute) and was left for 24 hours. Then the viscosity was measured.

3. Measurement

The viscosity measurement is carried out in the same glass flask with the Brookfield-Viscosimeter RVT, Aerometer 10, with heliopath at 10 rpm.

4. Computation

Read scale values x factor = viscosity in mPas.

It should be noted that DE - OS 31 14 493 corresponds to U.S. patent application Ser. No. 852,595 filed Apr. 16, 1986.

DE - OS 12 93 138 corresponds to U.S. Pat. No. 3,433,593.

We claim:

1. A precipitated silica having, the following physical-chemical features:

| | | |
|---|---|---|
| drying loss (DIN 53198) | % | 3-7 |
| Conductivity at 25° C. (4% slurry) | µS | 400-800 |
| pH level (5% accd. to DIN 53200) |  | 6-7 |
| BET* surface area (DIN 66131) | $m^2/g$ | 130-150 |
| tamping density (DIN 53194) | g/l | 100-150 |
| macropore volume D > 30 nm (by Hg-injection method) | ml/g | 3.2-4/0 |
| Gardner oil absorption | ml/100 g | 180-200 |
| water retention capacity | % | 76-79 |
| Cu abrasion | mg | 5-14 |
| RDA** abrasion |  | 35-100 |
| REA*** abrasion |  | 40-90 |
| scratch |  | little-very little |
| viscosity (in 16% glycerin-water dispersion (1:1); aerometer D w/ heliopath) | mPas | 5000-10000 |
| Fe content | ppm | 240-280 |

2. A process for the production of the precipitated silica as in claim 1 which has the following physical-chemical features:

| | | |
|---|---|---|
| drying loss (DIN 53198) | % | 3-7 |
| conductivity at 25° C. (4% slurry) | µS | 400-800 |
| pH level (5% acd. to DIN 53200) |  | 6-7 |
| BET* surface area (DIN 66131) | m2/g | 130-150 |
| tamping density (DIN 53194) | g/l | 100-150 |
| macropore volume D > 30 nm (by Hg injection method) | ml/g | 3.2-4.0 |
| Gardner oil absorption | ml/100 g | 180-200 |
| water retention capacity | % | 76-79 |
| Cu abrasion | mg | 5-14 |
| RDA** abrasion |  | 35-100 |
| REA*** abrasion |  | 40-90 |
| scratch |  | little-very little |
| viscosity | mPas | 5000-10000 |

-continued (in 16% glycerin-water dispersion
(1:1); aerometer D w/ heliopath)
Fe content                    ppm        240-280

*BET—Brunauer-Emmett-Teller equation. for surface area determination in study of sorption
**RDA—Radioactive Dentin Assay
***REA—Radioactive Enamel Assay comprising, (A) producing a thickened precipitated silica suspension by reaction of an alkali silicate solution with an acid while avoiding formation of a gel,
in which the acid and the alkali silicate solution are fed into an aqueous alkali silicate solution reaction medium at selected solution concentrations and selected flow velocities while maintaining a precipitation temperature of between 80° C. and 90° C. in the reaction medium to thereby precipitate silica,
said reaction medium having an initial viscosity value,
said aqueous alkali silicate solution reaction medium having a concentration of approximately 5 to 25 g of $SiO_2$ per liter of solution,
thereby holding the viscosity of the reaction medium uniformly low for a time period of at least 30% of the total precipitation time,
and the pH of the reaction medium is held between 10 and 12,
the viscosity of the reaction medium thereafter increasing as a result of the reaction up to a maximum value,
terminating the feed of the reaction components before the viscosity of the reaction medium following passage through said maximum value has dropped to a point less than 100% above the initial viscosity,
adding sulfuric acid to adjust the pH of the reaction medium to below 7, to thereby obtain a thickening precipitated silica,
(B) producing an abrasive precipitated silica suspension by first precipitating silica from a selected alkali silica solution reaction medium with a concentration of about 5-25 g of $SiO_2$ per liter solution
by adding to said solution reaction medium an acid and alkali metal silicate solution
while maintaining a precipitation temperature in the reaction medium of between 80° C. and 90° C.,
said reaction medium having an initial viscosity value, the viscosity of the reaction medium being uniformly low during a time period of at least 30% of the total precipitation time by control of addition of said acid and silicate solution,
maintaining the pH level between 10 and 12,
terminating the addition of the acid and alkali silicate solution, before the viscosity of the reaction medium after passing through a maximum falls to a level less than 100% above the initial viscosity,
adjusting the pH level with sulfuric acid to 7 to 9, diluting with hot water to a precipitated silica content of 10-30 g/l and sodium sulfate content of 6-20 g of $Na_2SO_4$/l,
heating to 80° C.-90° C.,
and while holding this pH level constant simultaneously adding alkali metal silicate solution, sulfuric acid and hot water, for a precipitation time of from 15 to 180 minutes, to obtain a precipitated silica final concentration of from 40 to 80 g/l,
acidifying the suspension with sulfuric acid to a pH of below 7, mixing the two precipitated silica suspensions (A) and (B) thoroughly,
and recovering a combined precipitated silica and then comminuting with an air jet mill.

3. A precipitated silica having the following physical-chemical features:

| | | |
|---|---|---|
| drying loss (DIN 53198) | % | 3-7 |
| conductivity at 25° C. (4% slurry) | μS | 250-400 |
| pH level (5% accd. to DIN 53200) | | 6-7 |
| BET surface area (DIN 66131) | m2/g | 220-250 |
| tamping density (DIN 53194) | g/l | 80-120 |
| macropore volumes D > 30 nm (by Hg injection method) | ml/g | 3.2-4.0 |
| Gardner oil absorption | ml/100 g | 200-220 |
| water retention capacity | % | 77-78 |
| Cu abrasion | mg | 8-12 |
| RDA abrasion | | 60-80 |
| REA abrasion | | 60-90 |
| scratch | | little |
| viscosity (in 16% glycerin-water-dispersion (1:1); aerometer D w/ heliopath) | mPas | 14000-18000 |
| Fe content | ppm | 70-90 |

4. A process for the production of a precipitated silica as in claim 3, which has the following physical-chemical features:

| | | |
|---|---|---|
| drying loss (DIN 53198) | % | 3-7 |
| conductivity at 25° C. (4% slurry) | μS | 250-400 |
| pH level (5% accd. to DIN 43200) | | 6-7 |
| BET surface area (DIN 66131) | m2/g | 220-250 |
| tamping density (DIN 53194) | g/l | 80-120 |
| macropore volumes D > 30 nm (by Hg injection method) | ml/g | 3.2-4.0 |
| Gardner oil absorption | ml/100 g | 200-220 |
| water retention capacity | % | 77-78 |
| Cu abrasion | mg | 8-12 |
| RDA abrasion | | 60-80 |
| REA abrasion | | 60-90 |
| scratch | | little |
| viscosity (in 16% glycerin-water dispersion (1:1); aerometer D with heliopath) | mPas | 14000-18000 |
| Fe content | ppm | 70-90 | comprising, (A) producing an abrasive precipitated silica suspension by providing an alkali silicate solution reaction medium with a concentration of approximately 5-25 g of $SiO_2$ per liter solution
adding to said reaction medium an acid and alkali metal silicate solution with selected solution concentrations and selected flow velocities,
while maintaining a precipitation temperature of between 80° C. and 90° C., in the reaction medium, said reaction medium having an initial viscosity value,
holding the viscosity of the reaction medium uniformly low and maintaining the pH level between 10 and 12 during a time period of at least 30% of the total precipitation time,
the viscosity of the reaction medium thereafter increasing up to a maximum value,
terminating the addition of the said acid and alkali metal silicate solution before the viscosity of the reaction medium following passage through said maximum value drops to a value less than 100% above the initial viscosity, adding sulfuric acid to adjust the pH to 7 to 9, the suspension thus obtained being diluted with hot water to a precipitated silica content of from 10-30 g/l and a sodium sulfate content of 6-20 g of $Na_2SO_4$/l, heating the suspension to 80° C.-90° C., and while holding this pH level constant simultaneously adding alkali metal silicate solution, sulfuric acid, for a precipitation time of from 15 to 180 minutes, to thereby obtain a precipitated silica final concentration of from 40 to 80 g/l, acidifying the suspension with sulfuric acid to a pH below 7 to thereby obtain an abrasive precipitated silica, and (B) providing a second precipitated silica suspension in which the precipitation is carried out in the strongly acidic pH range by simultaneous feed of sodium silicate and acid solution to reaction vessel containing at least one substance dissolved in water, which form soluble complexes with iron, and thereafter mixing the two precipitated silica suspensions (A) and (B) together, and recovering a combined precipitated silica and then thoroughly comminuting with an air jet mill.

5. The process of claim 4 wherein said second silica suspension if produced by a reaction with pH of 1.5 to 2.5.

6. The process of claim 2 wherein the two silica suspensions are mixed together in the ratio range of 1:2 to 2:1 based on the solids content.

7. The process of claim 5 wherein the two silica suspensions are mixed together in the ratio range of 1:2 to 2:1 based on the solids content.

8. The process of claim 2 wherein the acid is sulfuric acid and the alkali silicate is sodium silicate.

9. The process of claim 2 further comprising after mixing the two precipitated silicas, the resulting mixed silica is filtered out, washed, spray dried and comminuted in the air jet mill.

10. The process of claim 4 wherein the acid is sulfuric acid and the alkali silicate is sodium silicate.

* * * * *